(12) United States Patent
Sirat

(10) Patent No.: US 8,129,703 B2
(45) Date of Patent: Mar. 6, 2012

(54) INTRAORAL IMAGING SYSTEM AND METHOD BASED ON CONOSCOPIC HOLOGRAPHY

(75) Inventor: Gabriel Y. Sirat, Jerusalem (IL)

(73) Assignee: Optimet, Optical Metrology Ltd., Jerusalem (IL)

( * ) Notice: Subject to any disclaimer, the term of this patent is extended or adjusted under 35 U.S.C. 154(b) by 340 days.

(21) Appl. No.: 12/401,668

(22) Filed: Mar. 11, 2009

(65) Prior Publication Data

US 2009/0231649 A1 Sep. 17, 2009

Related U.S. Application Data

(60) Provisional application No. 61/035,894, filed on Mar. 12, 2008.

(51) Int. Cl.
*G01N 21/86* (2006.01)
*H01L 27/00* (2006.01)
*G03H 1/00* (2006.01)

(52) U.S. Cl. ............... 250/559.05; 250/208.1; 359/30

(58) Field of Classification Search .......... 359/22, 359/24, 25, 30–34, 402, 668, 495; 250/559.05–559.09, 559.19, 559.2, 559.44, 250/208.1
See application file for complete search history.

(56) References Cited

U.S. PATENT DOCUMENTS

| | | | |
|---|---|---|---|
| 3,692,414 A | 9/1972 | Hosterman et al. | |
| 4,136,949 A | 1/1979 | Hayamizu et al. | |
| 4,298,784 A | 11/1981 | Schmall | |
| 4,602,844 A | 7/1986 | Sirat et al. | |
| 4,744,664 A | 5/1988 | Offt et al. | |
| 4,976,504 A * | 12/1990 | Sirat et al. ................... 359/29 |
| 4,978,841 A | 12/1990 | Barrett et al. | |
| 5,081,540 A | 1/1992 | Dufresne et al. | |
| 5,081,541 A | 1/1992 | Sirat et al. | |
| 5,340,962 A | 8/1994 | Schmidt et al. | |
| 5,453,969 A | 9/1995 | Psaltis et al. | |
| 5,841,539 A | 11/1998 | Ikurumi et al. | |
| 5,953,137 A | 9/1999 | Sirat et al. | |

(Continued)

FOREIGN PATENT DOCUMENTS

DE 41 02 404 8/1992

(Continued)

OTHER PUBLICATIONS

Laurent M. Mugnier, Conoscopic holography: toward three-dimensional reconstructions of opaque objects; Applied Optics, vol. 34, No. 8, pp. 1363-1371, Mar. 10, 1995.

(Continued)

*Primary Examiner* — Georgia Y Epps
*Assistant Examiner* — Don Williams
(74) *Attorney, Agent, or Firm* — Sunstein Kann Murphy & Timbers LLP

(57) ABSTRACT

A conoscopic holographic system and a method for imaging a scene characterized by a surface having a three-dimensional shape. The system utilizes an optical source, which illuminates the scene with substantially linear distributions of light, and independent register of a plurality of elementary conoscopic holograms in the image plane. Each elementary conoscopic hologram represents the imaging of a single emitting point of the illuminated scene. The optical source is translated relative to the scene to generate a sequence of optical holograms, and a weighted reconstruction of the holograms is performed, in a computer process, at a median plane to devise the three-dimensional shape of the imaged scene.

22 Claims, 13 Drawing Sheets

U.S. PATENT DOCUMENTS

| | | | |
|---|---|---|---|
| 6,134,013 A | 10/2000 | Sirat et al. | 356/376 |
| 6,181,482 B1* | 1/2001 | Grafton | 359/670 |
| 6,423,933 B2 | 7/2002 | Nicholas et al. | |
| 7,375,827 B2 | 5/2008 | Sanilevici et al. | |
| 7,494,338 B2 | 2/2009 | Durbin et al. | |
| 7,705,970 B2* | 4/2010 | Piestun et al. | 356/4.01 |
| 2004/0100639 A1 | 5/2004 | Sung et al. | 356/605 |
| 2005/0234344 A1 | 10/2005 | Sanilevici et al. | |
| 2006/0023223 A1 | 2/2006 | Bennison | 356/457 |
| 2006/0227338 A1* | 10/2006 | Buchler et al. | 356/612 |
| 2007/0293769 A1 | 12/2007 | Doherty et al. | |
| 2008/0148590 A1* | 6/2008 | Hayashi et al. | 33/710 |
| 2008/0225393 A1* | 9/2008 | Rinko | 359/571 |
| 2009/0073419 A1* | 3/2009 | Gesner et al. | 356/73 |

FOREIGN PATENT DOCUMENTS

| | | |
|---|---|---|
| WO | WO 2007/102667 | 9/2007 |
| WO | WO 2009/063087 | 5/2009 |

OTHER PUBLICATIONS

I-mes GmbH, Point laser sensor CONOPROBE/Line laser sensor CONOLINE, reprint of product specification from http://www.i-mes-gmbh.com/englisch/downloads/cono_druck.pdf, 6 pages, downloaded Feb. 17, 2009.

Scheiber et al., Nuclear Medicine Image Registration by Spatially Noncoherent Interferometry; The Journal of Nuclear Medicine, vol. 41, No. 2, Feb. 2000, 8 pages.

Malet and Sirat, Conoscopic holography application: multipurpose rangefinders, J. Opt. 29, pp. 183-187 (1998).

International Searching Authority, International Search Report mailed Apr. 16, 2008 in a related application No. PCT/US2007/074608, 12 pages.

Sirat, G., "*Conoscopic holography. I. Basic principles and physical basis*", Journal of the Optical Society of America A, vol. 9, No. 1, pp. 70-83, Jan. 1992.

Mugnier, L., "*Conoscopic holography: toward three-dimensional reconstructions of opaque objects*", Applied Optics, vol. 34, No. 8, pp. 1363-1371, Mar. 10, 1995.

Sirat, et al., "*ConoProbe and ConoLine, two new 3-dimensional measurement systems*", Proc. of SPIE, vol. 4830, pp. 319-324, XP002418745, Jan. 2003.

European Patent Office, International Search Report, Int'l Appl. No. PCT/IL2009/000276, dated Jul. 20, 2009, 15 pages.

* cited by examiner

INTRAORAL IMAGING SYSTEM AND METHOD BASED ON CONOSCOPIC HOLOGRAPHY

CROSS-REFERENCE TO RELATED APPLICATIONS

The present application claims priority from U.S. Provisional Application Ser. No. 61/035,894 filed on Mar. 12, 2008, which is incorporated herein by reference in its entirety.

FIELD OF INVENTION

The present invention relates to non-contacting metrology, and, in particular, to an apparatus and methods for optical scanning and digitizing the coordinates of a solid body of complex shape, particularly within a confined space such as a person's mouth.

BACKGROUND ART

Determination of coordinates of points on the surface of an object is often used for digitizing or imaging of the object, or for various manufacturing applications. Some of the known coordinate-measuring probes are based on conoscopic holography.

The theory of conoscopic holography, a technique implementing interference of light (which may be spatially incoherent, unpolarized, and/or quasi-monochromatic) emanating from an object for the purposes of retrieving information about the shape of the object, has been developed by Gabriel Sirat et al. (see, e.g., JOSA A, v. 9, pp. 70-90, 1992, and references therein, all incorporated herein by reference). The use of spatially incoherent light makes it possible to use this technique in a large variety of environments. Moreover, the spatial resolution of conoscopic holography in conjunction with photodiode arrays provides for digital processing of the resulting holograms.

In the basic interference set-up, shown in FIG. 1, an object 1, illuminated with incident light, reflects the light (specularly and/or diffusely) within a solid angle A. The reflected light $r_i$ passes through a circular polarizer P1, thereby generating two beams $r_o$ and $r_e$ with mutually orthogonal polarizations (in phase quadrature), both of which (and ordinary and extraordinary polarizations, respectively) propagate through a uniaxial crystal 2 having a crystal axis 3, along approximately the same geometrical path. These two rays are converted back to the same polarization mode by a following circular analyzer P2, placed after the crystal 2, and so interfere in the observation (or recording) plane 4. The circular analyzer P2 also compensates for the initial quarter-wavelength delay that the ordinary and extraordinary beams acquire upon propagation through the circular polarizer P1. The interference pattern appearing in the observation plane 4 is a conoscopic hologram and represents a superposition of the conoscopic figures for each point 5 of the object 1. The conoscopic figures for each point 5 (or for a well-defined set of points) will be referred to herein as "elementary" conoscopic figures. Each elementary conoscopic figure is formed by interference of light emanating from a particular object point, and is shaped, in part, according to the position of the emitting object point relative to the fixed recording plane 4. Each point of the object creates its own conoscopic figure, which reveals the transverse position of the point (based on position with respect to the center of the pattern) and distance (based on the density of interferometric fringes). Thus, the conoscopic hologram contains complete information about distances between the emanating object points and the recording plane, and, therefore the object's spatial distribution.

Conoscopic holography, linear or quadratic, may be utilized in many applications such as quality control measurements, digitizing, reverse engineering and in-process inspection. Several methods of optical or numerical reconstruction of conoscopic holograms, allowing for the retrieval of information about the shape of an illuminated object, and the description of corresponding systems have been reported to-date. For example, laser sensors ConoProbe™ and Cono-Line™, developed by Optical Metrology Ltd. (Optimet) of Jerusalem, Israel (http://optimet.com/optimet_company_profile.htm) on the basis of conoscopic holography, provide contactless three-dimensional measuring of surfaces with submicron resolution. Conoscopic holography is the subject of various patents, including U.S. Pat. Nos. 4,602,844, 4,976,504, 5,081,540, 5,081,541, and 7,375,827, each of which is incorporated herein by reference. In particular, linear conoscopic holography and systems have been disclosed in U.S. Pat. No. 5,953,137, which is also incorporated herein by reference.

In applications such as dental surface profiling for purposes of reconstruction, orthodontics etc., the relative movement of the patient's mouth with respect to the sensor and other vibrations during the tooth-measurement cycle would impose practical limitations on performance of the existing systems which are not configured for operation within a human mouth. Clearly, an automated and robust solution to the problem of quick digitizing of complex bodies is desirable. It was also recognized in prior art that performing surface and distance measurements on translucent objects such as teeth with conventional techniques such as a three-dimensional automated scanning (see, e.g., WO 2007/071306 to Durbin et al.) results in projected images that are blurred because of the diffusion of light throughout the object. To overcome such limitation, prior art scanners employ opacifying the area of a scene to be imaged by applying an appropriate coating to it.

SUMMARY OF INVENTION

Embodiments of the invention provide methods for imaging a scene characterized by a surface having a three-dimensional shape. Such methods have steps of illuminating the scene so as to project onto the surface of the scene spatially-discontinuous distribution of light that defines an instantaneous elementary object, varying with time to produce successive elementary objects, and imaging such successive elementary objects through an optical coding module to form a sequence of conoscopic holograms of successive elementary objects. Further, the methods have a step of computing the three-dimensional shape of the surface based upon the sequence of conoscopic holograms. In some embodiments the imaged scene may be interior to a mouth of a person, and illuminating the scene may include projecting a plurality of substantially linear distributions of light onto the scene. In specific embodiments a plurality of substantially linear distributions of light may be represented by equidistantly distributed lines of illumination.

According to other embodiments of the methods of the present invention, a source of illumination may be translated relative to the scene, which may be realized by delivering light through a plurality of optical waveguides such as optical fibers disposed in a fiber-bundle assembly, or through relay optics optionally including a periscope or a telescope.

In addition, imaging successive elementary objects through the optical coding module may include imaging successive elementary objects through a conoscope, and, in some embodiments, evaluation of the three-dimensional shape of the sample may comprise independently analyzing N elementary conoscopic figures, N being a number of lines in the plurality of lines of illumination, where each elementary conoscopic figure represents imaging of a single emitting point on a respective line from the plurality of lines of illumination. In specific embodiments of the invention, the evaluation of the three-dimensional shape of the surface of the scene from the sequence of conoscopic holograms may include evaluating three-dimensional shape of the surface of the scene from the sequence of exponential optical conoscopic holograms where a weighted reconstruction of real or exponential holograms is performed at a median plane.

Furthermore, the method of the invention may include imaging each successive elementary object without displacement thereof and with respective different polarization arrangements to form an elementary set of conoscopic holograms, and further comprise processing, in an external processing unit, digital representations of optical conoscopic holograms from the elementary set to remove a bias and a conjugate image.

Other embodiments of the invention provide for a conoscopic holographic system comprising an optical source providing a spatially-discontinuous distribution of light. Here, the conoscopic holographic system may further comprise a periscope projecting the spatially-discontinuous distribution of light to a scene characterized by a surface, and, in specific embodiments, project a plurality of substantially linear distributions of light thereon.

The system of other embodiments may comprise imaging optics configured to provide independent registration, in an image plane, of N elementary conoscopic figures. Optionally, each elementary conoscopic figure may represent imaging of a single emitting point on a respective substantially linear distribution of light from the plurality of substantially linear distributions of light, single emitting points being optical conjugates of photosensitive elements in a detector disposed in an image plane, the optical conjugates defined by the imaging optics. Some specific embodiments of the system of the invention may utilize anamorphic imaging optics.

Yet other embodiments provide methods for determining a distance to an illuminated surface with a linear conoscope, the linear conoscope characterized by an image plane and an optical axis, the illuminated surface being illuminated with N substantially spatially discontinuous distributions of light. Such methods entail several computer processes, wherein:

in a first computer process, representing an image signal measured in the image plane with a detector, as a weighted combination of N functions, each function representing an elementary signal contributed to the image signal by a corresponding single emitting point from the respective discontinuous distributions of light;

in a second computer process, for each of the single emitting points, correlating a weighted test function and the weighted combination to generate a correlation function, the weighted test function being weighted with a factor representing a lateral displacement of the respective single emitting point from the optical axis; and in a third computer process, for each of the single emitting points, determining a longitudinal separation between the image plane and the respective emitting point from a maximum of the correlation function.

BRIEF DESCRIPTION OF THE DRAWINGS

The foregoing features of the invention will be more readily understood by reference to the following detailed description taken with the accompanying drawings, in which.

DEFINITION OF TERMS

Figure 1:
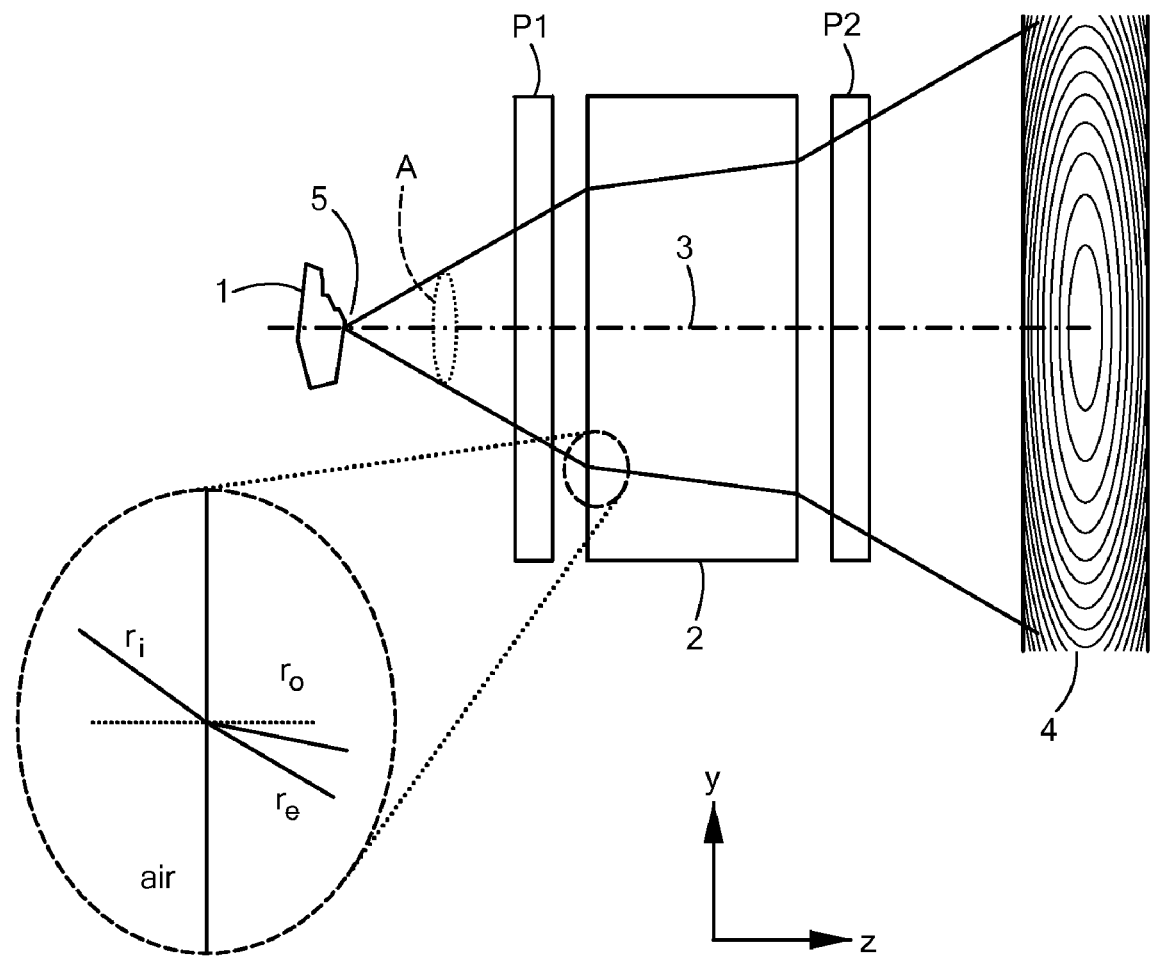
FIG. 1 depicts the principal features of a prior art conoscopy system.

Unless context otherwise requires, in the description of the invention and accompanying claims the following terms will have meanings as defined below:

| Term | Definition |
| --- | --- |
| Intra-oral three-dimensional camera | a system able to characterize or image a tooth, a group of teeth or a complete jaw using an optical system introduced in the mouth of a patient |
| Measurement Space | A Cartesian spatial frame referenced to a predefined fixed point of the system, the origin |
| Object | a physical object to be measured. Much information exists describing and defining the object such as shape, color, texture, etc. |
| Illumination Module | a physical module projecting a predetermined three dimensional light distribution, namely, the illumination light distribution |

| Term | Definition |
|---|---|
| Elementary Pattern | an elementary pattern is the projection of the illumination light distribution on the x, y plane; in accordance with certain embodiments of the present invention, the elementary pattern may constitute a small number of discrete lines along the y axis, for example. |
| Illuminated Object | an intersection of the illumination light distribution with the object; in practice it may represent stripes on the object, for example. |
| Optical Coding Module | an optical coding module is a physical module transforming the Illuminated Object into an optical conoscopic hologram. It is typically built from crystals and lenses |
| Optical Conoscopic Hologram | a two-dimensional optical light distribution which retains information of the three-dimensional shape of the object. It is a coded version of the three-dimensional data. |
| Compound conoscopic hologram | a mathematical combination of several optical conoscopic holograms obtained by multiple values of a physical parameter. For example, the subtraction of two optical conoscopic holograms in which, in the second one, an additional optical path difference of half a wavelength had been added creates a compound conoscopic hologram without bias. Bipolar and quasi-complex conoscopic holograms have been described in the French patent FR 8817225 |
| Digital Conoscopic Hologram | a mathematical representation of the optical conoscopic hologram obtained by recording on a detector the light intensity, digitizing the resulting analog electronic signal and storing the result in a matrix on a computer or signal processing hardware |
| Detector Module | an optoelectronic apparatus performing the retrieval of the digital conoscopic hologram from the optical conoscopic hologram |
| Reconstruction Algorithm | a set of mathematical procedures able to retrieve an evaluation the shape of the object - or of the illuminated object for a discriminating illumination - from its digital conoscopic hologram |

DESCRIPTION OF SPECIFIC EMBODIMENTS OF THE INVENTION

Hardware Modules of Embodiments of the Invention

In accordance with certain embodiments of the present invention, a conoscopic profilometer is provided, i.e., a device for determining the distance from a fiducial reference point to each of a set of points on a specified surface. Some of the disclosed embodiments are particularly suited for intraoral dental measurements. Typical component parts of a conoscopic profilometer in accordance with the present invention are now described with reference to FIG. 2A.

An illumination module 8 of a conoscopic profilometer is an optical or optomechanical assembly, described in detail below, that generates a spatially-discontinuous light pattern and projects it upon the surface of the object to be measured. As used herein and in any appended claims, "spatially-discontinuous" denotes a pattern in which at least two non-contiguous points are illuminated in a plane transverse to the illuminating beam. The illumination module 8 may include a semiconductor laser in conjunction with a holographic transmission mask or any other means of generating a specified pattern of illumination. In some embodiments, the spatially-discontinuous pattern of light may be in form of a series of substantially linear distributions of light 10 as presented schematically in FIG. 3. To produce such light distribution, the conoscopic profilometer of the invention preferably utilize a blue-wavelength laser diode (e.g., 405 nm), as compared to 650-685 nm sources conventionally utilized in commercial conoscopic systems. As a result of working at such shorter wavelength, the system of the invention provides, among other advantages, higher surface density of information about the measured object (up to 50% more information, since the surface resolution increases as $\sim 1/\lambda^2$).

Figure 2A:
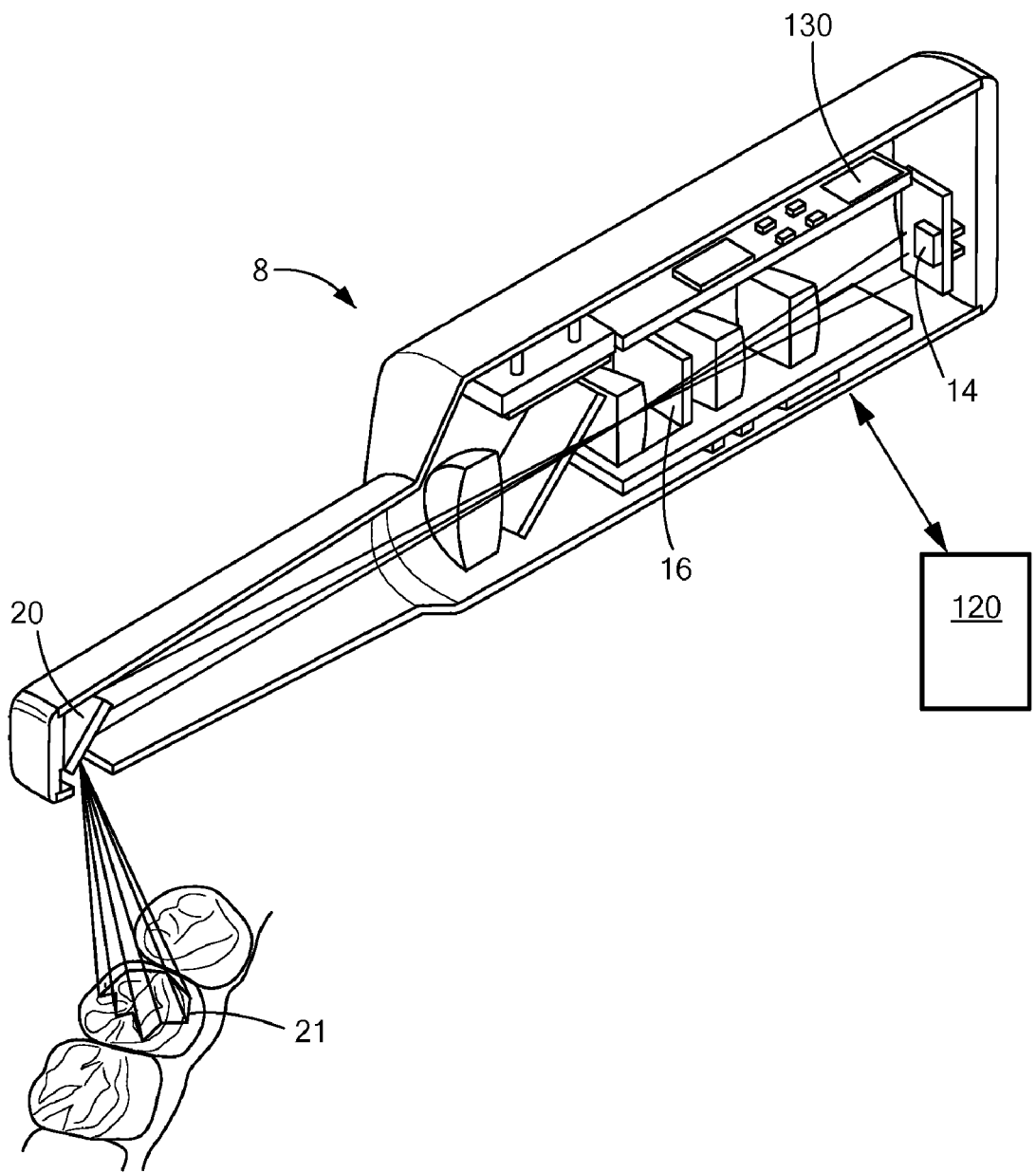
FIG. 2A is a cutaway view of a conoscopic profilometer in accordance with an embodiment of the present invention.
Figure 3:
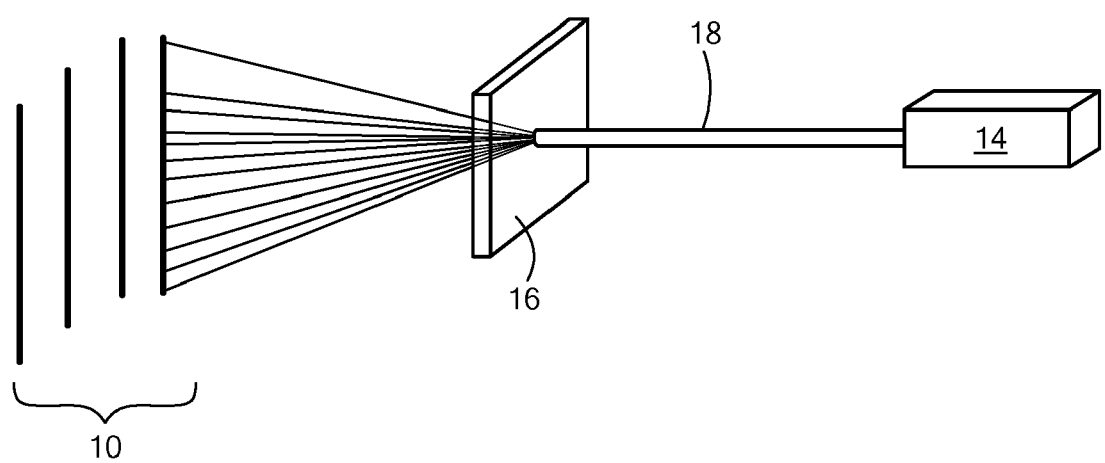
FIG. 3 depicts an illumination modality in accordance with a further embodiment of the present invention.

In reference to FIGS. 2A and 3, a schematically shown illumination module 8 of an embodiment of the invention generally includes, therefore, a laser 14 equipped with appropriate imaging optics and an adequate optical or holographic component 16 (array generator, or beam shaper, in FIG. 3) adapted to create a line array pattern 10 in the far field. It would be understood, however, that different patterns of illumination such as, for example, a grid of emitting points, can also advantageously be employed in different embodiments of the invention.

The array generator 16, which may also be referred to as a beam shaper, modifies the wavefront of the incident laser beam 18 to a wavefront with specified irradiance and phase profiles, achieved, in some embodiments, with efficiency exceeding 90%. In embodiments utilizing digital optics for the array generator, the single incident laser beam may be diffracted by a digital optical element to produce multiple output beam distribution with specified uniformity and number of beams (or number of illumination lines per mm in the observation plane with predetermined length, width etc). In a specific embodiment, for example, an array generator comprised of a digital optical element can produce a predetermined number of highly uniform equidistantly distributed, sparse stripes or lines of illumination with variation of irradiance, among equidistant lines, of less than <10% and less than 2% energy remaining in a zeroth order of diffraction.

Figure 2B:
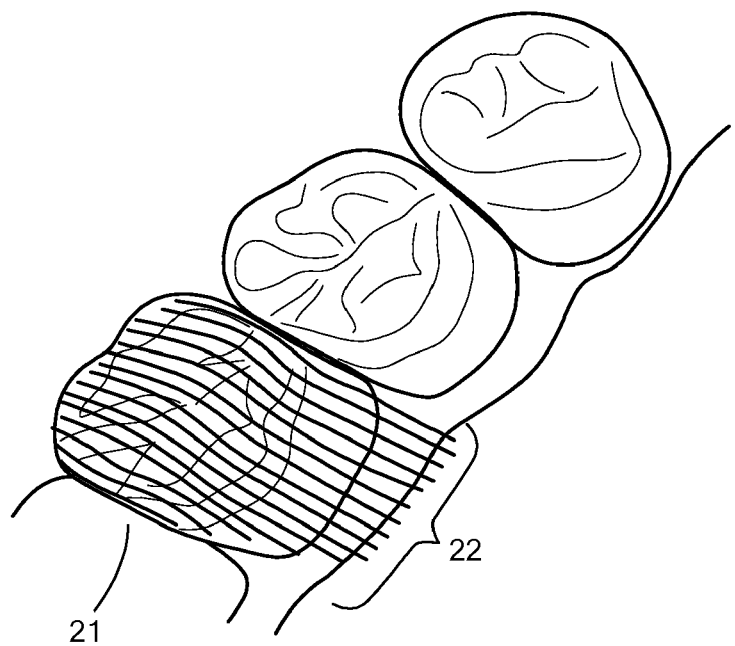
FIG. 2B shows the surface irradiation of a tooth in accordance with an embodiment of the present invention.

An objective assembly, in some specific embodiments of the invention may include a periscope in order to allow the system to be conveniently inserted in the patient mouth. Due to the co-linearity of conoscopic holography, conoscopic sensors are capable of accommodating various relay optics such as telescopes or periscopes. As shown in FIGS. 2A and 2B, a periscopic component of the objective may be represented by a folding mirror 20, delivering equidistantly distributed stripes or lines of illumination to an intraoral scene 21 to irradiate a surface of a tooth. A portion of the surface of the scene, illuminated through the objective at any moment in time, defines an instantaneous elementary object 22.

A translator module (not shown) may be employed with a purpose of shifting the spatially-discontinuous light distribution relative to the illuminated scene (surface of the object) in order to optically sample the surface of the object. As a result of a repeated pre-determined shift of illuminating light pattern with respect to the object, a succession of elementary objects is formed that is imaged through the optical coding module to form a sequence of conoscopic holograms of successive elementary objects, holograms being further analyzed to evaluate three-dimensional shape of the object. Such analysis includes a merging process that involves further repositioning and transforming of each of the successive conoscopic holograms into a cloud of points which are then merged using a merging algorithm. The merging process provides data about the overall shape of the object, and merging of reconstructed surfaces utilizing a cloud of points is known in the art.

Realization of embodiments of the translator module may vary. For example, while keeping the laser 14 stationary within the profilometer 8, the illuminating beam 18 may be displaced with respect to the array generator 16 or the object to be measured with as rotating mirror or optical wedge or prism. Alternatively, a micropositioning stage can be employed to translate the laser relative to the scene. Or, the delivery of laser light to the array generator 16 may be instead realized through a plurality of optical waveguides. Other specific embodiments may utilize, for example, optical fibers disposed in a fiber-bundle assembly, such as a fiber bundle assembly of N fibers that are lit sequentially.

An optical coding module is employed in various of the embodiments of the profilometer of the invention, and transforms the light from every point of the instantaneous elementary object, into an elementary optical conoscopic hologram, thereby producing in the observation plane, for each instantaneous elementary object, a composite conoscopic hologram which is an interferometric image representing a superposition of multiple elementary conoscopic holograms. A typical optical coding module of the invention is generally similar to an apparatus described in abovementioned patents and schematically illustrated in FIG. 1. It comprises an assembly of optical crystals, lenses and polarizers, and will not be described in further detail.

Figure 9:
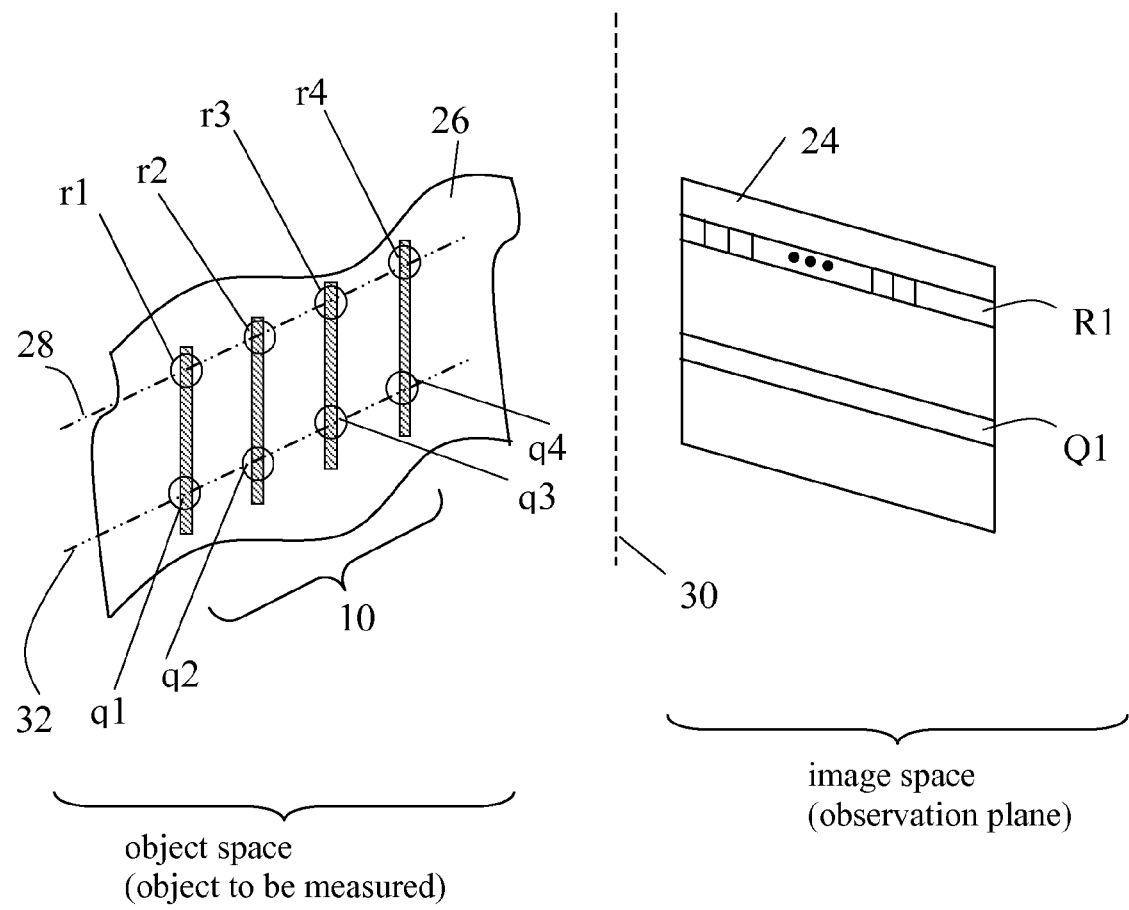
FIG. 9 schematically depicts the correspondence of a fraction of a conoscopic hologram produced by an instantaneous elementary object, in accordance with an embodiment of the present invention.

Each of the composite conoscopic holograms from the sequence of composite holograms, formed in the observation plane by the optical coding module as a result of the operation of the translator module, is further registered and digitized with a detector module, producing digital representations of conoscopic holograms. In some of the embodiments, a detector may be a CCD or CMOS matrix with standard resolution (VGA or Megapixel), such as a sufficiently sensitive at the operational wavelength Kodak KAI-340, for example, providing resolution of 648*484 pixels and a frame rate of 120 Hz. According to embodiments of the invention, the detector module is equipped with an anamorphic optical system configured to provide for independent registration of the conoscopic holograms produced by each elementary-object subset, defined as an optical image of a specific row of pixels in a CCD in object space, onto that uniquely corresponding row of pixels. This concept is schematically illustrated in FIG. 9, where each pixel in a pixel-row R1 of a detector 24 registers a corresponding fraction of a conoscopic hologram produced by only that portion of the instantaneous elementary object, formed by illuminating a surface of a scene 26 with the pattern 10 of equidistantly-spaced stripes of light, that intersects a linear region 28 defined as an optical conjugate of the row R1 by an optical system 30 of the embodiment of the invention. In other words, the anamorphic optics of the embodiment of the invention assure that only portions r1 through r4 contribute to the conoscopic hologram that will be viewed by the pixels of the detector row R1, which remains optically isolated from any other light emitted by any other portion of the instantaneous elementary object. Similarly, another row Q1 of pixels in the CCD 24 receives interfering light only from areas q1 through q4, located at intersections of an optical conjugate 32 of the row Q1 with the illumination pattern 10. To optimize the registration of interferometric information with the detector module, the optical system of the invention is configured to deliver a corresponding conoscopic hologram to each row of the detector.

In addition, the conoscopic profilometer may be equipped with an external processing unit 120 (shown in FIG. 2A) that provides signal-processing hardware capable of retrieving the information about the shape of the illuminated surface of the object from the digital conoscopic holograms or sparse reconstructions, the motion parameters, and the motion-corrected data of the shape of the instantaneous elementary object and data about the overall shape of the object provided by the merging algorithm. The external processing unit 120 may include a computer. Embodiments of the conoscopic profilometer of the invention may also be supplemented with a telemetry unit 130, which includes required electronic hardware and software supporting data transfer and controlling functions of the conoscopic profilometer 8 and the external processing unit 120.

Examples of Certain Embodiments of the Invention.

Figure 10:
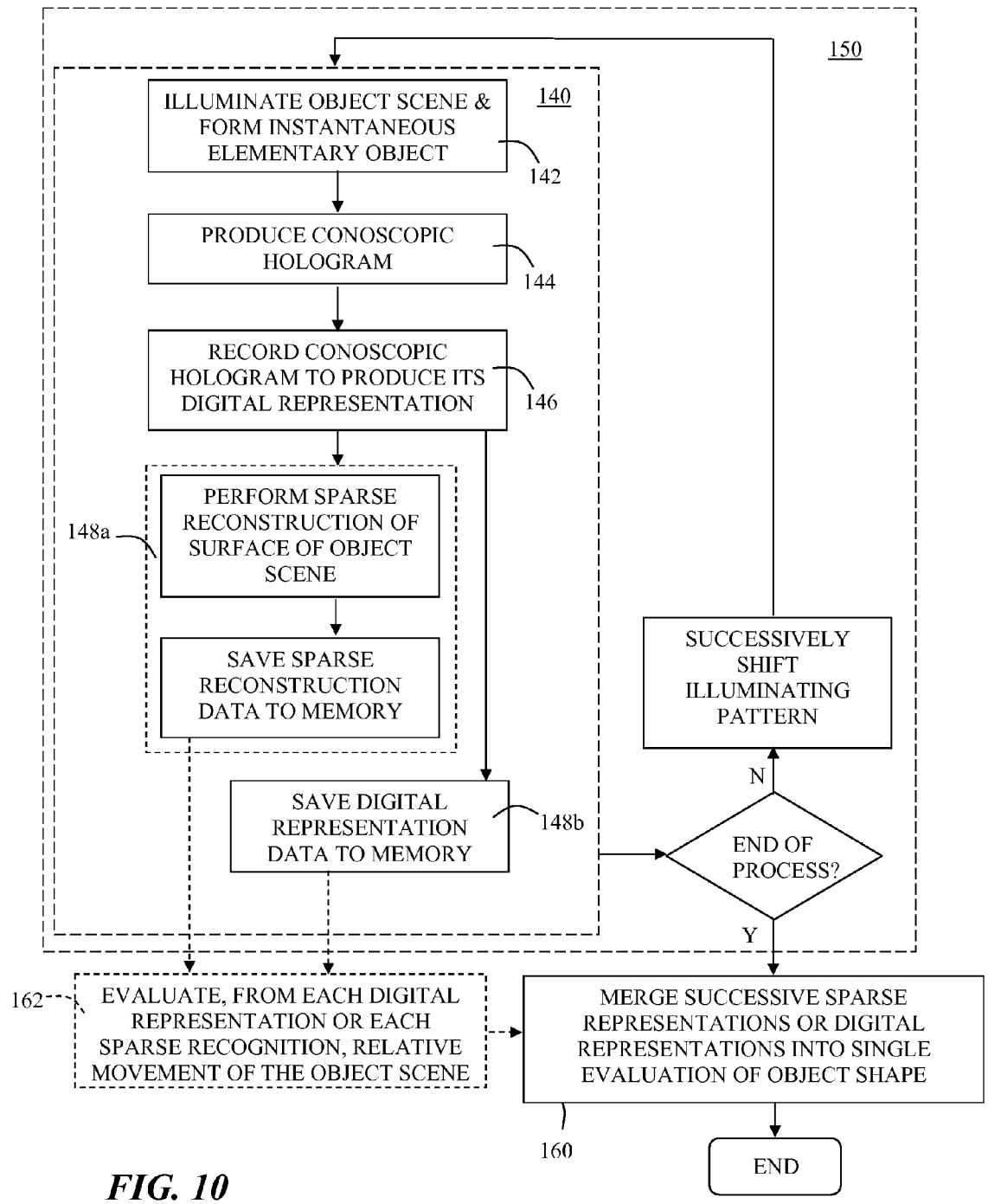
FIG. 10 is a flowchart depicting a conoscopic measurement with elementary acquisition, full acquisition, and merging processes, in accordance with an embodiment of the present invention.

As an illustration, now described with reference to the flowchart of FIG. 10, an intraoral measurement with the use of a conoscopic profilometer, according to one embodiment of the current invention, may comprise elementary acquisition, full acquisition, and merging processes.

In an elementary optical acquisition process 140, the intraoral scene may be, at step 142, illuminated with a pattern consisting, for example, of 16 lines separated from each other by about 1 mm with 480 illuminating points per line and forming a single instantaneous elementary object that produces, at step 144, a conoscopic hologram representing a sparse view of the entire object being measured, such as a tooth. The full view of the entire object by each elementary acquisition, even if carried out with sparse resolution, enables retrieving parameters of the relative movement of the object in reference to the sensor. Typical dimensions of such an optical hologram in the observation plane may be, for example, 16×17 mm$^2$. At step 146, the elementary optical conoscopic hologram is recorded by the detector module to produce a digital conoscopic hologram which is a digital representation of the optical hologram.

According to one embodiment of the invention, the system may further perform, at step 148a, sparse reconstruction of the surface of the illuminated intraoral scene by retrieving from the digital conoscopic hologram (with then use of a reconstruction algorithm of the invention) evaluation data representing the shape of the illuminated surface. Alternatively, at step 148b, the system may keep a digital representation of the elementary optical conoscopic hologram for further processing. The data corresponding to the digital conoscopic holograms or the sparse reconstructions is stored on an appropriate storage medium, such as a computer memory.

The full optical acquisition is further accomplished at step 150 through combining N displaced and interlaced elementary acquisitions by appropriately shifting the illuminating pattern with the translator module so as to shift a successive elementary conoscopic hologram in the observation plane by, for example, an integer number of CCD-pixels with respect to the previous hologram. In some embodiments, shifting the abovementioned illumination pattern by 75 μm with respect to the imaged scene within a fraction of a second may produce a succession of 12 elementary objects in 12 steps over 1 mm distance along the object's surface, as well as 12 respectively corresponding elementary optical conoscopic holograms registered by the detector in the observation plane with a one-pixel shift with respect to one another. In such embodiments, a lateral imaging resolution on the order of 50*100 μm² or better may be achieved.

Finally, in the merging process of step 160, either the successive sparse reconstructions or the successive digital representations are merged, using the merging process of the invention in the external processing unit, into a single set of data representing evaluation of the object shape.

Optionally, a registration algorithm may be used, which allows to evaluate, from each digital conoscopic hologram or from each sparse reconstruction, the relative movement of the object itself that occurred during the process of measurement of the object's shape, as shown in phantom line at step 162. Here, the movement compensation algorithm repositions, if necessary, the results of each elementary acquisition relative to a global system of coordinates (such as, for example, Cartesian) using the solid movement parameters previously retrieved by the movement evaluation algorithm.

In some embodiments, a set of several (e.g., two, three or four) elementary optical conoscopic holograms of the same instantaneous elementary object, formed by illumination of the scene with a spatially-discontinuous distribution of light, may be recorded sequentially, in different polarization arrangements, without displacement of the elementary object by shifting the illuminating pattern with respect to the scene. Processing the data corresponding to several optical conoscopic holograms of the same elementary object formed with light having different polarization may be required to eliminate parasitic information collected from a coherent continuous background (also referred to as bias) and to a conjugate image. Recording of the set of holograms in different polarizations maybe accomplished, for example, by using, an appropriate light valve switch such as the one described in French patent 88-17225, or U.S. Pat. No. 5,081,541 to Sirat et al., each of which is incorporated herein in its entirety. Varying-polarization-based means of elimination of bias and conjugate-image related data have been earlier described in U.S. Pat. No. 5,081,541.

Algorithms of the Embodiments of the Invention

The conoscopic hologram is an optical light distribution which retains, in a two-dimensional format, full information of the three-dimensional shape of the object. A general exponential conoscopic hologram, as defined and described by G. Sirat (in *JOSA A*, v. 9, p. 73, 1992) contains all the three-dimensional information of a convex object with the same size and resolution. It is, therefore, mathematically equivalent to the reconstructed convex object, making the mathematical problem solvable.

Due to the presence of noise of physical and digital origin, the data retrieved from the hologram of the full object suffer from drawbacks and inaccuracies. Algorithms for retrieval and restoration of the data such as those described by L. M. Mugnier (see "Conoscopic holography: toward three-dimensional reconstructions of opaque objects", *Appl. Opt.*, v. 34, pp. 1363-1371, 1995) are known in the art but are not necessarily robust and require iterative solutions.

To simplify the mathematical problem and to make the results more accurate and robust, the number of independent variables must be reduced. To that end, the abovementioned commercial systems ConoProbe™ and ConoLine™, for example, restrict the measurement of the object to a single point from each line of data through illuminating the object with light emanating from a single point (ConoProbe™) or a single line (ConoLine™). However, these systems are quite slow, because they record a full line for each measurement point or a full frame for a single line. In particular, in the ConoProbe™, a single point illuminates the entire array; in the ConoLine™, appropriate optics is used in order to separate, in the second transverse dimension, the contribution from different points of the line of illumination to separate rows in a CCD-array.

The IntraOral system implementing the current invention is fast enough and does not compromise the metrological quality of conoscopic sensors. The embodiments of the system utilize a multipoint scheme in which several different points of the same line of illumination from the set of substantially equidistantly distributed lines are recorded at once. The embodiments do not require imaging of a full continuous surface of the object, thus increasing the redundancy of information about the object's surface stored in the compound conoscopic hologram and reducing the complexity of the required algorithmic solution.

In the IntraOral 3-D Camera of certain embodiments of the present invention, for each row of pixels in a CCD, 8 to 16 illuminated object points are projecting light to the same detector pixel row, and the light on the pixel is a superposition of the contribution of these points. The reconstruction algorithm has to perform first a separation of the contribution of each emitter point to the detector intensity, retaining a measurement metrological capacity equivalent or close to those of the ConoProbe™ or of the ConoLine™.

This problem represents a theoretically solvable, under-constrained mathematical problem because a number of emitting points and a number of free parameters is smaller than a number of pixels on the detector. A chosen algorithm must insure complete decorrelation of the signal and noise terms. The reconstruction algorithm of the invention is based on the general formalism developed by Sirat, Mugnier and coworkers (see, e.g., the abovementioned reference to Mugnier and reference therein). In comparison to the general formalism, however, which is applicable to analyzing continuous two-dimensional elementary object but not substantially linear elementary objects, the algorithm used in the embodiments of the invention allowing reconstruction of discrete points of substantially one-dimensional objects.

The algorithm is applied separately to data obtained from each line of the digital conoscopic hologram, referred to as a signal, performs a weighted reconstruction of the exponential hologram at a median plane, situated at the middle of the measuring range. and processes a datum obtained from each emitting point of the instantaneous elementary object separately. At wavelengths where the material of the scene is at least partly translucent (i.e., permitting light to penetrate through the surface but diffusing it), the algorithms of the invention filters out the data associated with object reflections originating beyond the surface of the scene based on, among other factors, the known properties of the material.

The mathematical problem, therefore, is to retrieve longitudinal positions and energy in a conoscopic hologram from a small number of points the lateral positions of which are known. For the case of a one-dimensional exponential hologram, the one-dimensional distribution of intensity in the image plane $S(x)$ is $$S(x) = \sum_{i=1}^{N} A_i \exp[j\alpha_i(x-x_i)^2 + \varphi_i(\alpha_i)] \quad (1)$$

where S(x) is the signal intensity measured at each frame; $A_i$ and $\alpha_i$ are the unknown parameters defined below, $\alpha_i$ being a function of longitudinal position of each point characterized by a lateral position $x_i$, and $x_i$ and $\phi_i(x)$ are parameters measured during and known from the system calibration.

Embodiments of the current invention adapt three strategies to solve the abovementioned mathematical problem, among which are a modified Sirat-Mugnier algorithm (wave-reconstruction formalism), Time Frequency algorithms, and Maximum Likelihood Expectation approach.

(1) Reconstruction Algorithm: Wave Propagation Formalism

The reconstruction algorithm is applied separately to each line of the digital conoscopic hologram, referred to as a signal. The analysis of each line is performed separately, and, as a result, the mathematical two-dimensional problem is transformed to N sets of one-dimensional data, with N being the number of lines in the hologram, thus greatly reducing the number of variables and removing the continuity uncertainty of a general unknown pattern.

The light intensity reflected by each point of the elementary object, which is defined by illuminating the surface of the scene with a plurality of equidistantly distributed stripes or lines of light, the points having the same position on the respective line, produce a pattern on one column of the matrix expressed by:

$$I(x) = \sum_i A_i [\cos(\alpha_i(x-x_i))]^2 \quad (2)$$

Or, more generally, through an exponential function as described in Eq. (1) above, where $\alpha_i$ is a function of z, z being the longitudinal distance between the observation plane and the respective emitting point, $A_i$ is the irradiance produced by the emitting point, and $X_i$ is the point's lateral position with respect to the geometrical axis of the profilometer.

Figure 4A:
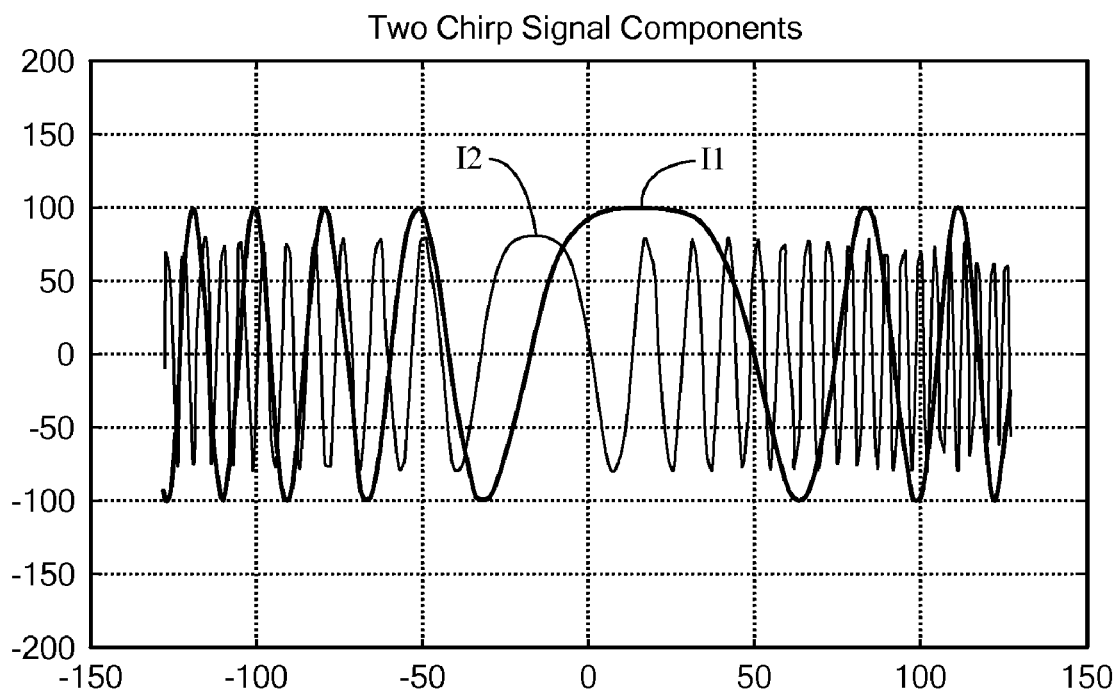
FIG. 4A illustrates two quadratically-chirped distributions of irradiance in the observation plane corresponding to two discrete object points.
Figure 4B:
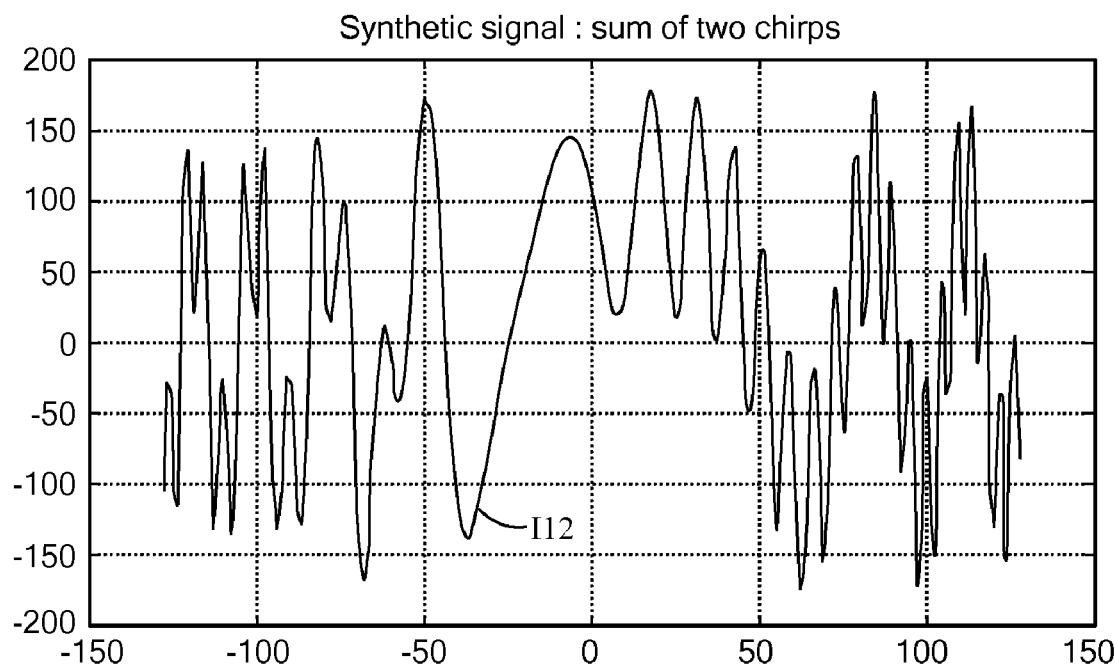
FIG. 4B is a compound hologram of the signals of FIG. 4A.
Figure 5A:
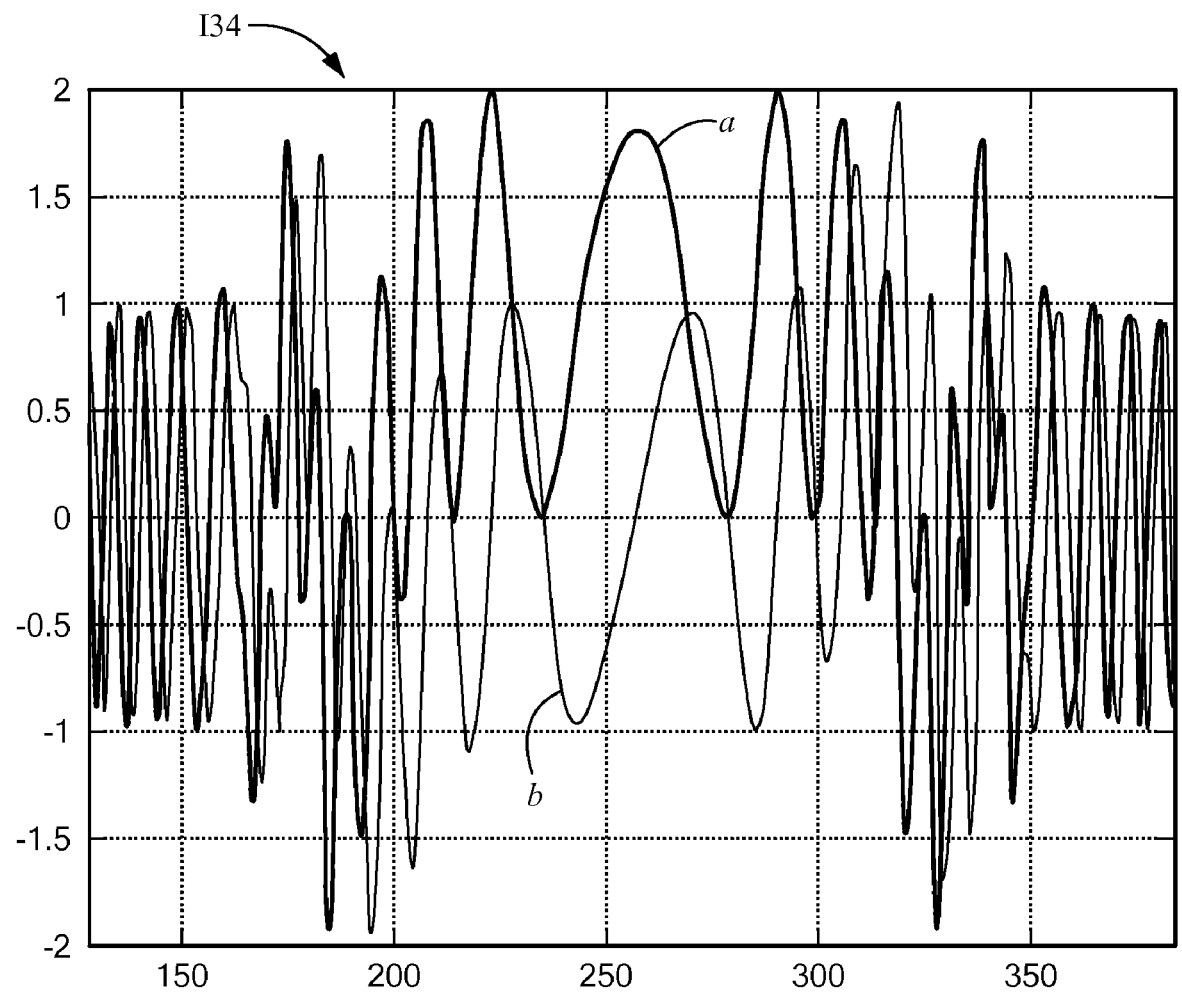
FIGS. 5A and 5B show, respectively, compound interferometric distributions recorded in the observation plane, in accordance with embodiments of the present invention.
Figure 5B:
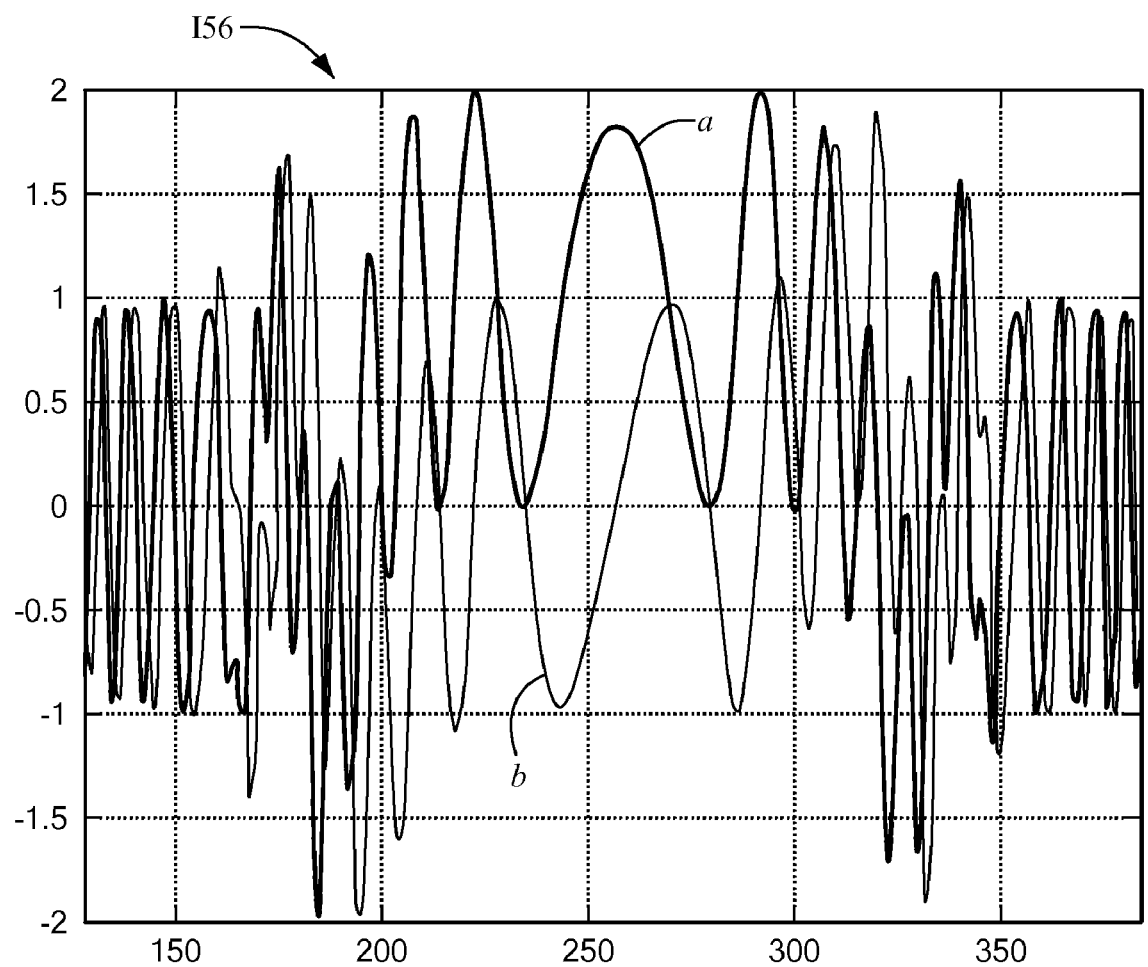

In embodiments with a telecentrically designed optical coding module, $x_i$ is constant; for non-telecentric design $x_i$ varies with distance z according to a known function. The compound optical hologram signal would correspond to a discretized signal represented by a sum (superposition) of N (where, in some embodiments, N=16) quadratically-chirped irradiance signals associated with optical conoscopic holograms formed by discrete emitting points. A quadratic chirp, corresponding to linear modulation of spatial frequency of the corresponding irradiance distribution in the observation plane, is proportional to z, while position of the center of the interferometric pattern is descriptive of a position of the corresponding emitting object point in xy-plane. As an example, FIG. 4A illustrates two quadratically-chirped distributions of irradiance in the observation plane, I1 and I2, respectively corresponding to two discrete emitting object points, E1 and E2 (not shown), that are shifted laterally with respect to the geometrical axis of the quadratic conoscope of the invention. As would be understood by one skilled in the art, the distances between the two points and the observation plane are different (i.e., $z_1 \neq z_2$), as follows from the different numbers of fringes in corresponding interferometric distributions. FIG. 4B represents a compound hologram I12 corresponding to distributions I1 and I2 of FIG. 4A and shows a superposition of the two signals in the observation plane. FIGS. 5A and 5B show, respectively, compound interferometric distributions (optical conoscopic holograms) I34 and I56, recorded in the observation plane and respectively formed by light emanating from respectively corresponding pairs of object points, (E3, E4) and (E5, E6), not shown. The emitting points in either pair are shifted laterally and symmetrically from the geometrical axis of the conoscope by 24 pixels. However, while E3 and E4 are equidistant from the observation plane (individual distributions I3 and I4, not shown, contain 64 fringes each), E5 and E6 are located at different distances (individual distributions I5 and I6, not shown, contain 60 and 64 fringes, respectively). As shown in each of FIGS. 5A and 5B, traces a represent real parts of the respective distributions, while traces b correspond to the imaginary parts.

Figure 6A:
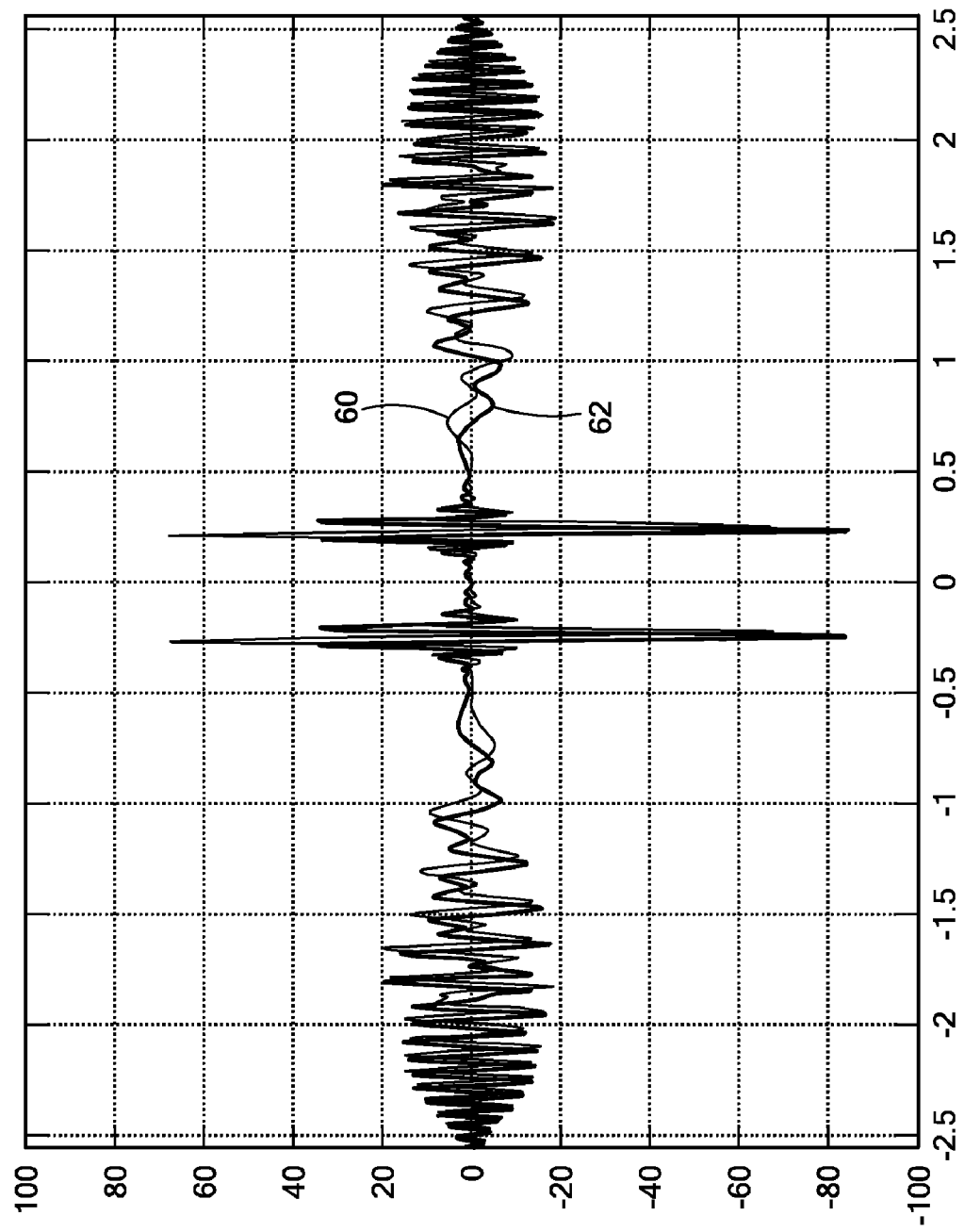
FIGS. 6A-6C illustrate the results of reconstruction of the compound holograms of FIGS. 5A and 5B.
Figure 6B:
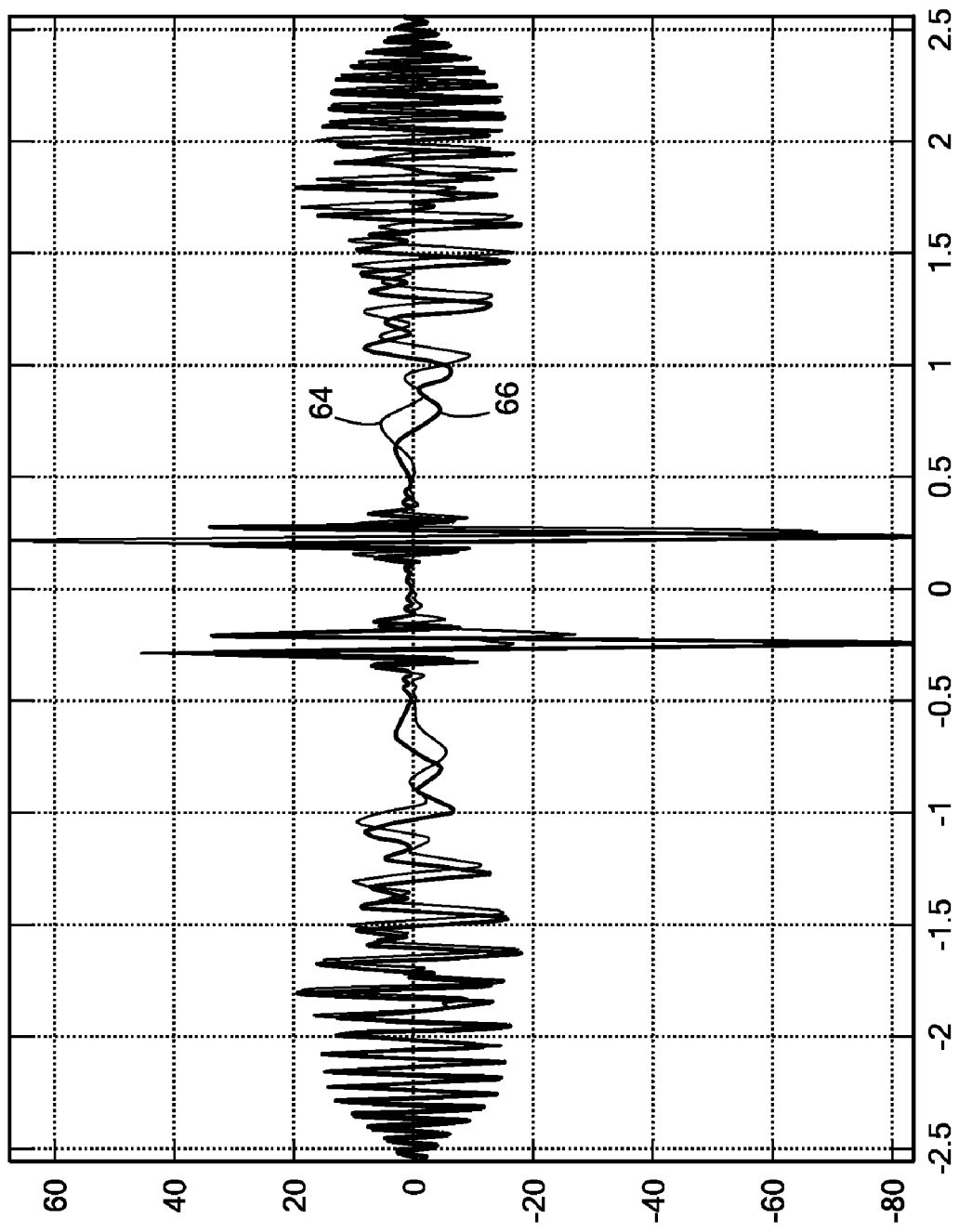
Figure 6C:
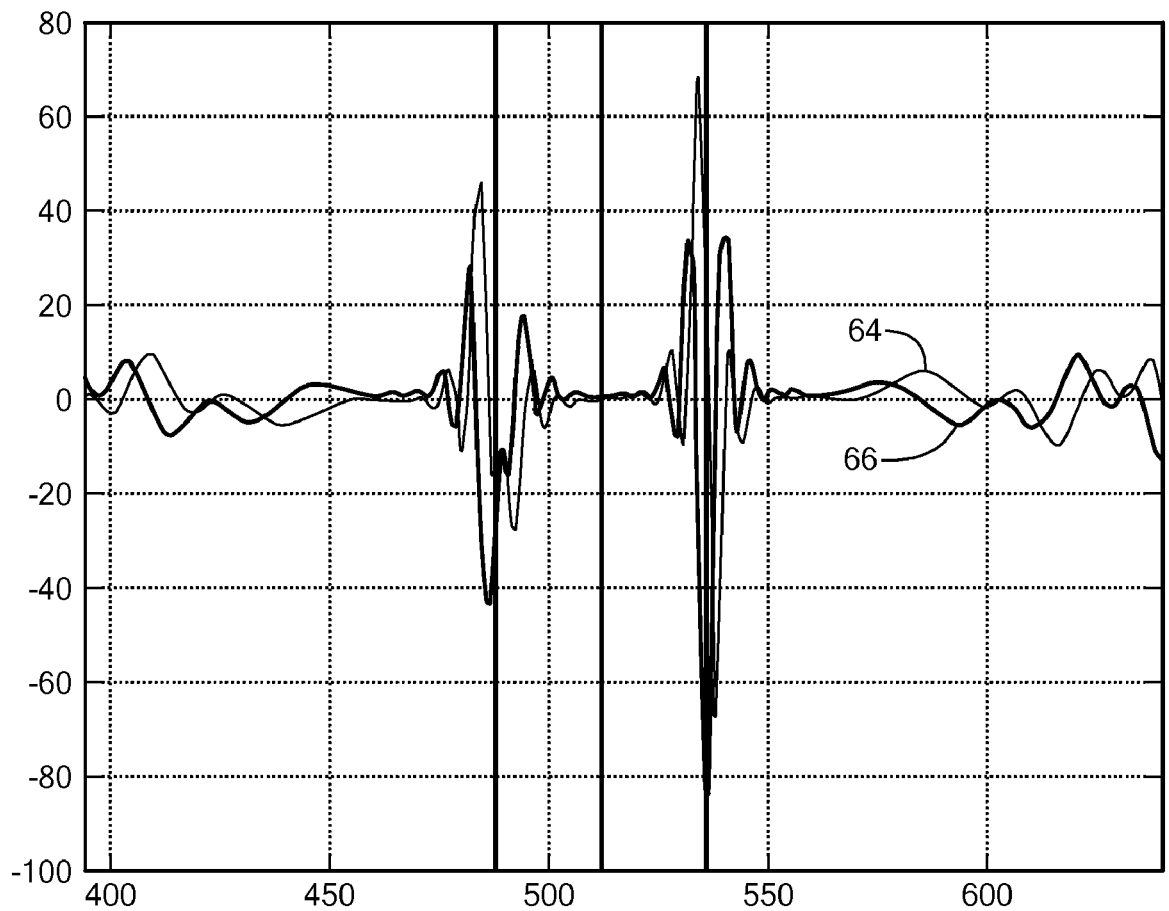

The algorithm reconstructs the two holograms in a median plane, in which the contributions of the two signals are separated spatially, and processes separately each one of the signals separately. Signal processing is performed by removing a real part of the holographic data and applying a Wiener-filter to the imaginary part. FIGS. 6(A. B, C) illustrate the results of reconstruction of the compound holograms of FIGS. 5A and 5B, respectively. In FIGS. 6A and 6B, signals 60, 62 and 64, 66 associated with corresponding object points are well separated and the spurious interference is optimized in the central portions of the reconstruction patterns (although they are still present in the peripheral regions). FIG. 6C, which is a zoom-in of FIG. 6B, shows the disappearance of the spurious interference in the region of the signals.

In a modified Sirat-Mugnier reconstruction algorithm, S(x) of Eq. (1) is correlated with m weighted exponential functions $$T_{mn}(x) = (x-x_n)\exp[j\alpha_m(x-x_n)^2 + \phi_{mn}] \quad (3)$$

and, for each emitting point n, the correlating figures $U_{mn}$ $$U_{mn} = \int (x-x_n)T_{mn}(x)S(x) \quad (4)$$

are analyzed, where $(x-x_n)$ is a lateral displacement of emitting point n from the optical axis of the conoscope. The maximal value $U_{mn}$ represents the best correlation, and, therefore, corresponds to the optimally determined longitudinal distance associated with parameter m. To increase precision of determination of the longitudinal distance, additional parabolic fitting is performed, corrected by interference effects. In doing so, to $U_{mn}$ by intensity in the n−1 and n+1 points is appropriately considered. This embodiment of the algorithms of the invention differs from the original Sirat-Mugnier two-dimensional algorithm, described in the above-referenced article by Mugnier, by a multiplier $(x-x_n)$. The need for the additional multiplier would be understood from the energy distribution in each cycle. In 2D, the energy present in a cycle is equal to the energy present in another cycle due to the equation of the surface of a ring. To reach the equivalent condition in 1D we need to add a linear weighting function.

(2) Reconstruction Algorithm: Time-Frequency Formalism

In the Time-Frequency algorithm, first a general Time Frequency algorithm is applied to data; additionally, the unknowns $A_i$ and $\alpha_i$ are retrieved parametrically from the 2D Time-Frequency surface using known parameters $x_i$ and $\phi_i(x)$.

Figure 7A:
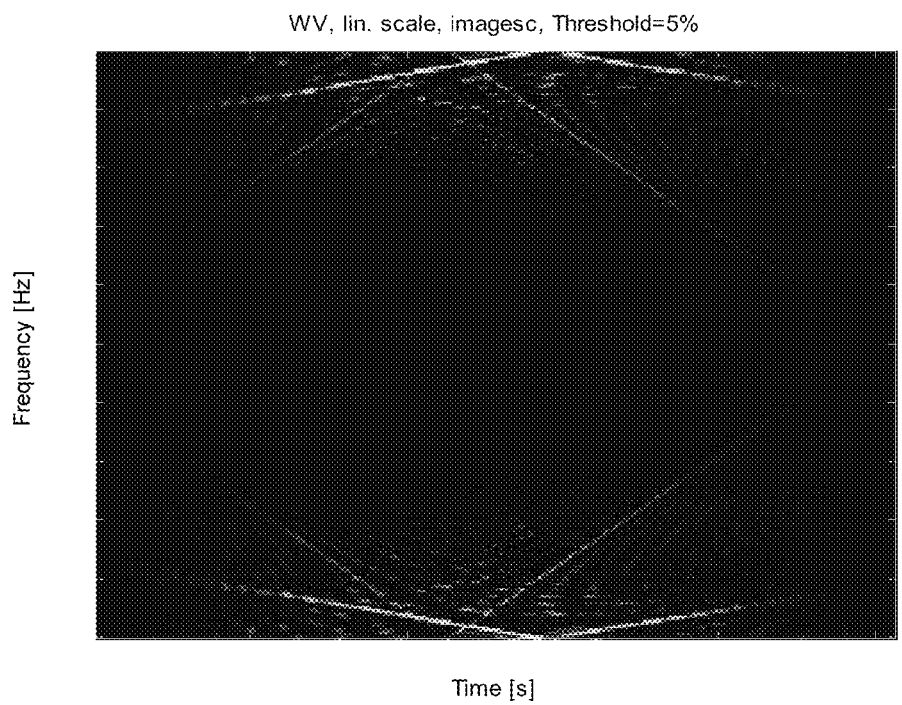
FIGS. 7A and 7B show Wigner-Ville filtered distributions and a short-term Fourier Transform, respectively, of the distributions of FIG. 4A.
Figure 7B:
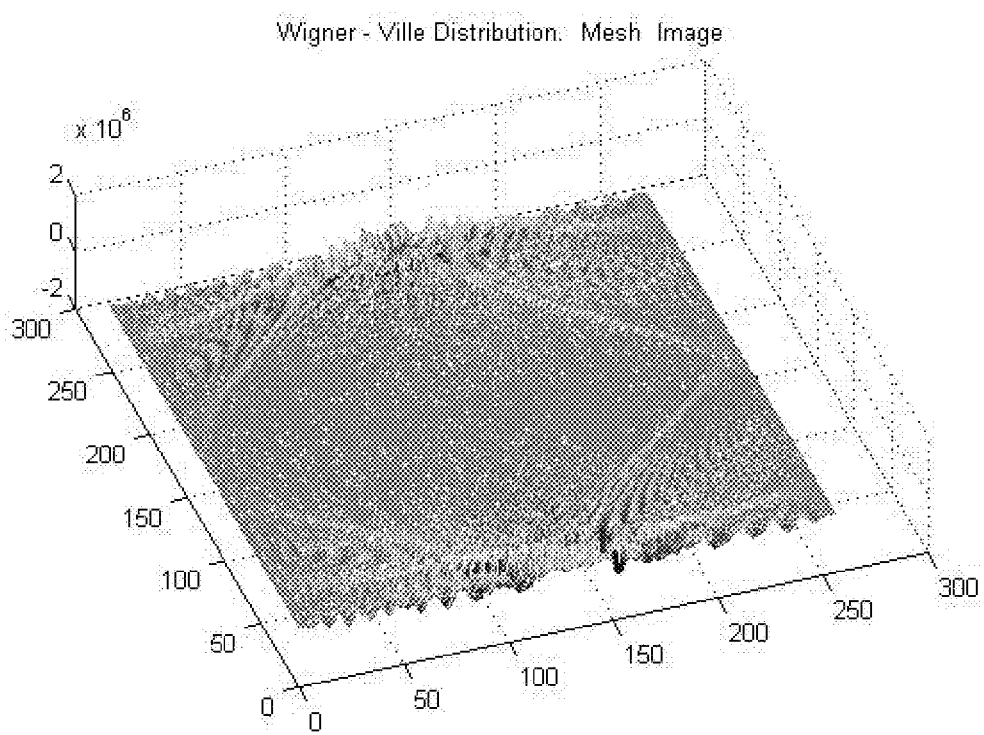

Several time-frequency algorithms for signal processing are known in the art, such as, for example, Wigner-Ville distribution or the short-term Fourier Transform. FIGS. 7(A, B) respectively represent a two-dimensional and three-dimensional views of the Wigner-Ville transform of the distributions I1 and I2 of FIG. 4A, which readily demonstrate two symmetric line-patterns.

(3) Reconstruction Algorithm: Maximum Likelihood Approach

Finally, in determining $A_i$ and $\alpha_i$ through the Maximum Likelihood Expectation approach, the results of one of the previous algorithms can be used as a starting point to minimize the search space for parameters $A_i$ and $\alpha_i$.

(4) Registration Algorithm (Repositioning and Merging)

The registration algorithm of preferred embodiments of the current invention is based on the continuous measurement of the relative position of the object with respect to the instrument. The algorithm may rely only on the recorded data, without recourse to any additional external references however the use of a separate mechanism for establishing relative displacement is also within the scope of the present invention.

Figure 8:
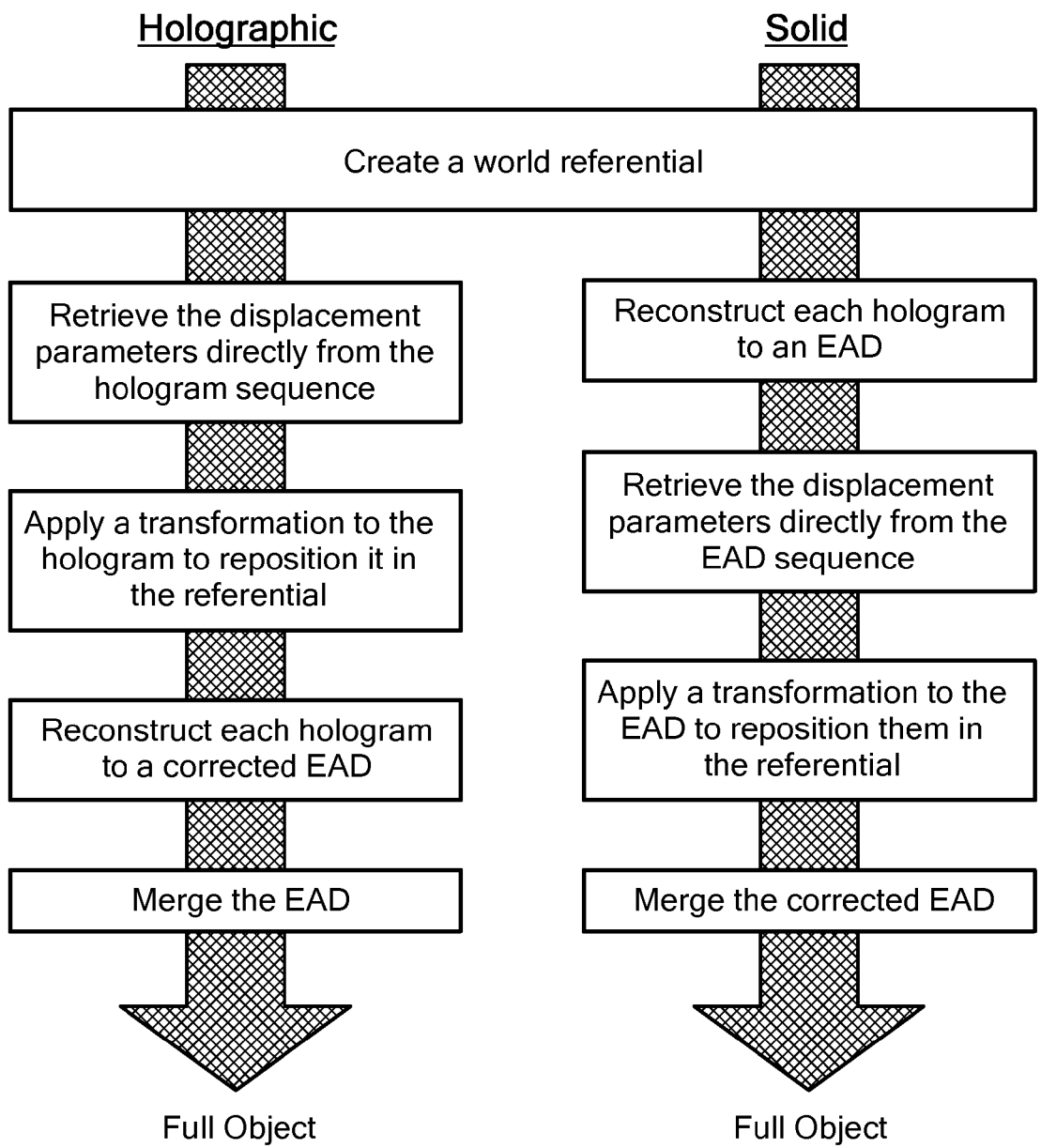
FIG. 8 is a flow chart depicting two alternate concepts of a registration algorithm in accordance with embodiments of the present invention.

The registration algorithm utilizes a linear differential from frame to frame. In a examplary profiling of the scene at a rate of about 10 mm per 1 sec, the scanning speed will be approximately constant (within about 25%, below 20 μm volumetric change from frame to frame). The view of the full object, in each elementary acquisition provides a larger basis for the calculation of the relative movements of the object itself. In one implementation, the global position parameters can be directly retrieved from the hologram differences. FIG. 8 illustrates two alternative concepts of the registration algorithm in accordance with embodiments of the present invention. Algorithms for merging the reconstructed surfaces utilizing a cloud of points are known in the art.

Measuring Objects Made of Translucent Materials

In the context of this disclosure, as discussed above and unless required otherwise, optically measuring a three-dimensional object implies measuring the spatial position of a light distribution, created by an adequate source of illumination, at the physical object. Assuming that object is opaque, the light-reflecting surface of is the outer physical surface of the object. This assumption is valid for most objects, but fails for those that are semi-transparent or translucent objects. The light penetrates the physical surface boundary of a translucent object down to the depth that defines what is known in the art as "skin layer." Consequently, the reflected light emerges not only from the surface points but also from a spatial region positioned below the surface. In other words, each illuminated point at the surface of the translucent object there is a group of points in the depth of the object that are also illuminated, thus effective broadening the size of the light distribution serving as an instantaneous elementary object for embodiments of the system of the invention. For translucent materials characterized by some absorbance figure, the intensity of light distribution within the object is depth dependent, and an average penetration depth can be used to characterize such dependency.

It would be understood that the conoscopic systems, where the strength of the reflected by the object signal is proportional to the cosine of the longitudinal position of the illuminated spot of the object, are ideally fitted to work with translucent materials. In such systems, the penetration-depth-dependent light distribution resembles the surface light distribution of Eq. (2) up to a second order of magnitude $O(z_0^2)$ in a variable $z_0$ related to a weighted average of the longitudinal position z:

$$\int_{z_0-\Delta z}^{z_0+\Delta z} I(z)\cos(\alpha z)dz = \cos(\alpha z_0)\int_{z_0-\Delta z}^{z_0+\Delta z} I(z)dz + O(z_0^2) \quad (5)$$

It is understood that operation of the embodiments of the invention requires programmable computer instructions, configuration, and support embodying all or part of the functionality previously described with respect to the invention and loaded onto a computer. Those skilled in the art should appreciate that such computer instructions and support can be written in a number of programming languages for use with many computer architectures or operating systems. For example, some embodiments may be implemented as entirely software (e.g., a computer program product) in a procedural programming language (e.g., "C") or an object oriented programming language (e.g., "C++"). Furthermore, such instructions may be stored in any memory device, such as semiconductor, magnetic, optical or other memory devices, and may be either transmitted to the computer using any communications technology (such as optical, infrared, microwave, or other transmission technologies) or embedded in it in a form of a programmable hardware chip with a computer program product fixed in it. It is expected that such a computer program product may be distributed as a removable storage medium with accompanying printed or electronic documentation (e.g., shrink wrapped software), preloaded on the computer (e.g., on a computer ROM or fixed disk), or distributed from a server or electronic bulletin board over the network (e.g., the Internet or World Wide Web). Of course, some embodiments of the invention may be implemented as a combination of both software and hardware. Still other alternative embodiments of the invention can be implemented as pre-programmed entirely hardware elements.

The embodiments of the invention heretofore described are intended to be merely exemplary and numerous variations and modifications will be apparent to those skilled in the art, including various combinations of four different methods that have been described. All such variations and modifications are intended to be within the scope of the present invention as defined in any appended claims.

What is claimed is:

1. A method for imaging a scene characterized by a surface having a three-dimensional shape, the method comprising:
    a. illuminating the scene so as project onto the surface of the scene a plurality of light stripes from a source of illumination, the plurality of light stripes defining an instantaneous elementary object, the instantaneous elementary object varying with time to produce a succession of elementary objects;
    b. imaging the succession of elementary objects through an optical coding module to form a sequence of conoscopic holograms, each conoscopic hologram respectively corresponding to an elementary object from the succession of the elementary objects; and
    c. computing the three-dimensional shape of the surface based upon the sequence of conoscopic holograms.

2. A method according to claim 1, wherein the scene is interior to a mouth of a person.

3. A method according to claim 1, wherein the surface includes translucent material.

4. A method according to claim 1, wherein illuminating the scene includes varying a relative position between the source of illumination and the scene.

5. A method according to claim 4, wherein varying the relative position includes translating a source of illumination relative to the scene.

6. A method according to claim 1, wherein illuminating the scene further comprises delivering light from a source of illumination through a plurality of optical waveguides.

7. A method according to claim 6, wherein the optical waveguides include optical fibers disposed in a fiber-bundle assembly.

8. A method according to claim 1, wherein illuminating the scene includes illuminating the scene through relay optics.

9. A method according to claim 8, wherein illuminating the scene includes illuminating the scene through a periscope.

10. A method according to claim 8, wherein illuminating the scene includes illuminating the scene through a telescope.

11. A method according to claim 1, wherein imaging the successive elementary objects through the optical coding module includes imaging the successive elementary objects through a conoscope.

12. A method according to claim 1, wherein evaluating the three-dimensional shape of the surface of the scene further comprises independently analyzing N elementary conoscopic figures, N being a number of lines in the plurality of lines of illumination, each elementary conoscopic figure representing imaging of a single emitting point on a respective line from the plurality of lines of illumination.

13. A method according to claim 1, wherein evaluating the three-dimensional shape of the surface of the scene from the sequence of conoscopic holograms includes evaluating three-dimensional shape of the surface of the scene from the sequence of exponential optical conoscopic holograms.

14. A method according to claim 13, further comprising a weighted reconstruction of exponential holograms at a median plane.

15. A method according to claim 1, wherein imaging the successive elementary objects through the optical coding module to form the sequence of optical conoscopic holograms of the succession of elementary objects includes imaging a successive elementary object without displacement thereof and with respective different polarization arrangements to form an elementary set of conoscopic holograms.

16. A method according to claim 15, further comprising processing, in an external processing unit, digital representations of optical conoscopic holograms from the elementary set to remove a bias and a conjugate image.

17. A conoscopic holographic system comprising:
an optical source;
an array generator for providing a plurality of light stripes;
a detector array for registering a plurality of conographic holograms based on the light stripes; and
a processor for measuring a distance from a specified point on a surface of a body to a fiducial reference position based on the plurality of conographic holograms and for generating a signal representing the distance.

18. A conoscopic holographic system according to claim 17, further comprising a periscope projecting the plurality of stripes of light onto a scene characterized by a surface.

19. A conoscopic holographic system according to claim 17, further comprising imaging optics configured to provide independent registration, in an image plane, of N elementary conoscopic figures.

20. A conoscopic holographic system according to claim 19, wherein each elementary conoscopic figure represents imaging of a single emitting point on a respective substantially linear distribution of light from the plurality of substantially linear distributions of light, single emitting points being optical conjugates of photosensitive elements in a detector disposed in an image plane, the optical conjugates defined by the imaging optics.

21. A conoscopic holographic system according to claim 19, wherein the imaging optics are anamorphic.

22. A method for determining a distance to an illuminated surface with a linear conoscope, the linear conoscope characterized by an image plane and an optical axis, the illuminated surface being illuminated with N substantially linear distributions of light, the method comprising:
in a first computer process, representing an image irradiance measured in the image plane with a detector as a weighted combination of N functions, each function representing an elementary signal contributed to the image irradiance by a corresponding single emitting point from a respective linear distribution of light;
in a second computer process, for each of the single emitting points, correlating a weighted test function and the weighted combination to generate a correlation function, the weighted test function being weighted with a factor representing a lateral displacement of the respective single emitting point from the optical axis; and
in a third computer process, for each of the single emitting points, determining a longitudinal separation between the image plane and a respective emitting point from a maximum of the correlation function.

* * * * *